United States Patent
Renfrew et al.

[19]

[11] Patent Number: 5,885,431
[45] Date of Patent: Mar. 23, 1999

[54] MICROGELS FOR USE IN MEDICAL DIAGNOSIS AND METHODS OF MAKING AND USING SAME

[75] Inventors: John A. Renfrew, Burlington; Paul Waterhouse, Copetown; John K. Stevens, Toronto; Henryk Zaleski, Niagara Falls, all of Canada

[73] Assignee: Visible Genetics Inc., Toronto, Canada

[21] Appl. No.: 836,269

[22] PCT Filed: Oct. 31, 1995

[86] PCT No.: PCT/US95/14531

§ 371 Date: May 1, 1997

§ 102(e) Date: May 1, 1997

[87] PCT Pub. No.: WO96/13717

PCT Pub. Date: May 9, 1996

Related U.S. Application Data

[63] Continuation-in-part of Ser. No. 332,577, Nov. 1, 1994, Pat. No. 5,627,022, and a division of Ser. No. 332,577, Nov. 1, 1994, Pat. No. 5,627,022.

[51] Int. Cl.[6] .................................................. G01N 27/26
[52] U.S. Cl. ........................... 204/466; 204/615; 204/465; 204/606; 204/620
[58] Field of Search .................................... 204/465, 466, 204/467, 456, 606, 615, 617, 618, 619, 620

[56] References Cited

U.S. PATENT DOCUMENTS

| | | | |
|---|---|---|---|
| 4,567,246 | 1/1986 | Gajria et al. | 526/318.44 |
| 4,811,218 | 3/1989 | Hankapiller | 364/413.01 |
| 4,823,007 | 4/1989 | Hanson | 250/327.2 |
| 4,863,647 | 9/1989 | Baylor, Jr. et al. | 264/22 |
| 4,929,329 | 5/1990 | Danby et al. | 204/299 R |
| 4,971,677 | 11/1990 | Kambara et al. | 204/299 R |
| 5,047,135 | 9/1991 | Nieman | 204/299 R |
| 5,062,942 | 11/1991 | Kambara et al. | 204/299 R |
| 5,073,246 | 12/1991 | Chu et al. | 204/299 R |
| 5,091,652 | 2/1992 | Mathies et al. | 250/458.1 |
| 5,092,973 | 3/1992 | Zare et al. | 204/182.1 |

(List continued on next page.)

FOREIGN PATENT DOCUMENTS

| | | |
|---|---|---|
| 2273783 | 6/1994 | United Kingdom . |
| 93/00583 | 1/1993 | WIPO . |
| 93/00986 | 1/1993 | WIPO . |

OTHER PUBLICATIONS

Ansorge et al., "Thermally Stabilized Very Thin (0.02–0.3 mm) Polyacrylamide Gels for Electrophoresis", *J Chromatography* 202: 45–53 (1980).

Maurer et al., "Polyacrylamide Gel Electrophoresis on Micro Slabs" *Anal Biochem.* 46: 19–32 (1972).

*Primary Examiner*—Robert Warden
*Assistant Examiner*—Alex Noguerola
*Attorney, Agent, or Firm*—Oppedahl & Larson

[57] ABSTRACT

An electrophoresis microgel is formed in a gel holder. The gel holder comprises a top substrate, a bottom substrate and a spacer disposed between the top substrate and the bottom substrate. The spacer establishes a separation of from 25 to 250 microns between the top substrate and the bottom substrate. A gel compartment is formed by partially sealing the top substrate to the bottom substrate, while leaving an opening for the introduction of unpolymerized gel. The gel compartment is then filled with an unpolymerized gel, which is polymerized in the gel compartment. Electrodes may be printed on the substrates, may be contacts to an exposed edge of gel, or may be applied through windows cut into one of the substrates. One type of gel holder makes use of graded beads having a diameter of 25 to 250 microns slurried in an adhesive such as an acrylate adhesive as the spacer. The slurry is printed onto the surface of one or both substrates to form a spacer of the desired shape, and then hardened using heat or light. If desired, the spacer can establish lanes within the gel.

33 Claims, 8 Drawing Sheets

U.S. PATENT DOCUMENTS

| | | | |
|---|---|---|---|
| 5,119,316 | 6/1992 | Dam et al. | 364/498 |
| 5,122,345 | 6/1992 | Tabor et al. | 422/116 |
| 5,135,650 | 8/1992 | Hjerten et al. | 210/198.2 |
| 5,141,868 | 8/1992 | Shanks et al. | 435/288 |
| 5,164,066 | 11/1992 | Yetman et al. | 204/299 R |
| 5,186,807 | 2/1993 | Sanford et al. | 204/299 R |
| 5,192,412 | 3/1993 | Kambara et al. | 204/299 R |
| 5,209,831 | 5/1993 | MacConnell | 204/299 R |
| 5,228,971 | 7/1993 | Brumley, Jr. et al. | 204/299 R |
| 5,281,322 | 1/1994 | Antonette et al. | 204/299 R |
| 5,338,426 | 8/1994 | Shigeura et al. | 204/299 R |
| 5,365,455 | 11/1994 | Tibbetts et al. | 364/497 |
| 5,470,916 | 11/1995 | Righetti et al. | 525/296 |

SEQUENCE LISTING ( 1 ) GENERAL INFORMATION:

( i i i ) NUMBER OF SEQUENCES:2

( 2 ) INFORMATION FOR SEQ ID NO: 1:

( i ) SEQUENCE CHARACTERISTICS:
        ( A ) LENGTH:30
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: No ( x i ) SEQUENCE DESCRIPTION: SEQ ID NO:1:

ATCGGCTAAT CGGCTAATCG GCTAATCGGC     30

( 2 ) INFORMATION FOR SEQ ID NO: 2:

( i ) SEQUENCE CHARACTERISTICS:
        ( A ) LENGTH:31
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: No ( x i ) SEQUENCE DESCRIPTION: SEQ ID NO:2:

ATCGGCTAAT CGGCTAATCG GCTAATCGGC T     31

MICROGELS FOR USE IN MEDICAL DIAGNOSIS AND METHODS OF MAKING AND USING SAME

This application is a continuation-in-part and divisional of U.S. patent application Ser. No. 332,577 filed May 1, 1994, which is now U.S. Pat. No. 5,627,022.

BACKGROUND OF THE INVENTION

This application relates to microgels for use in medical diagnosis, especially for the sequencing of nucleic acids, and to methods of making and using such gels.

DNA sequencing may be carried out using automated systems designed for laboratory application. Methods and apparatus for sequencing of DNA are described in U.S. Pat. Nos. 4,811,218; 4,823,007; 5,062,942; 5,091,652; 5,119,316 and 5,122,345, which are incorporated herein by reference.

The general methodology employed in these systems involves breaking up the sample DNA using restriction endonucleases; amplifying (for example with PCR) the restriction fragment of interest; combining the amplified DNA with a sequencing primer which may be the same as or different from the amplification primers; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained. Analysis of fragments may be done by electrophoresis, for example on a polyacrylamide gel.

International Patent Publication No. WO93/00986 describes electrophoresis gels with a thickness of 25 to 250 microns. The gels are formed between two clamped-together plates, one of which is grooved to a depth equal to the desired gel thickness to form parallel tracks which are then filled with gel.

In performing a nucleic acid sequence analysis on a gel, the characteristics of the gel, including the size and thickness, impact the time and cost required to do the analysis. Since it is desirable to reduce the time and cost of sequencing analyses in order to improve the available of sequencing as a diagnostic tool, it would be advantageous to have a gel which permitted analysis of very small quantities of oligonucleotide fragments in a short period of time. It is an object of the present invention to provide such a gel.

It is a further object of the invention to provide single-use, disposable gel holders which are readily filled with gel to provide a gel for rapid analysis of small samples.

It is a further object of the present invention to provide a method of making gels which achieve high resolution of oligonucleotide fragments in a short period of time.

It is a further object of the invention to provide a method of evaluating a sample containing oligonucleotide fragments of various lengths.

SUMMARY OF THE INVENTION

These and other objects of the invention are achieved using an electrophoresis microgel formed in a gel holder. The gel holder comprises a top substrate, a bottom substrate and a spacer disposed between the top substrate and the bottom substrate. The spacer establishes a separation of from 250 micron or less, preferably 25 to 250 microns, between the top substrate and the bottom substrate. A gel compartment is formed by partially sealing the top substrate to the bottom substrate, while leaving an opening for the introduction of unpolymerized gel. The gel compartment is then filled with an unpolymerized or partially polymerized gel, which is polymerized in the gel compartment. Electrodes may be printed on the substrates, may be contacts to an exposed edge of gel, or may be applied through windows cut into one of the substrates.

A preferred embodiment of the invention makes use of graded beads having a diameter of 250 microns or less, preferably 25 to 250 microns, slurried in an adhesive such as an acrylic or ultraviolet-light activated adhesive or bonded to the substrate using a low-melting glass as the spacer. The slurry is printed onto the surface of one or both substrates to form a spacer of the desired shape, and then hardened using heat or light. If desired, adhesive or a low-melting glass containing solid particles can also be used to establish lanes within the gel.

The spacing between the substrates can also be established using a plurality of beads disposed on the surface of the substrates within the gel compartment. In this case, the edges can be scaled by adhesive, or by adhesive-coated plastic films of appropriate thickness. Particles may also be disposed both within the adhesive and within the gel compartment.

DETAILED DESCRIPTION OF THE INVENTION

Figure 1:
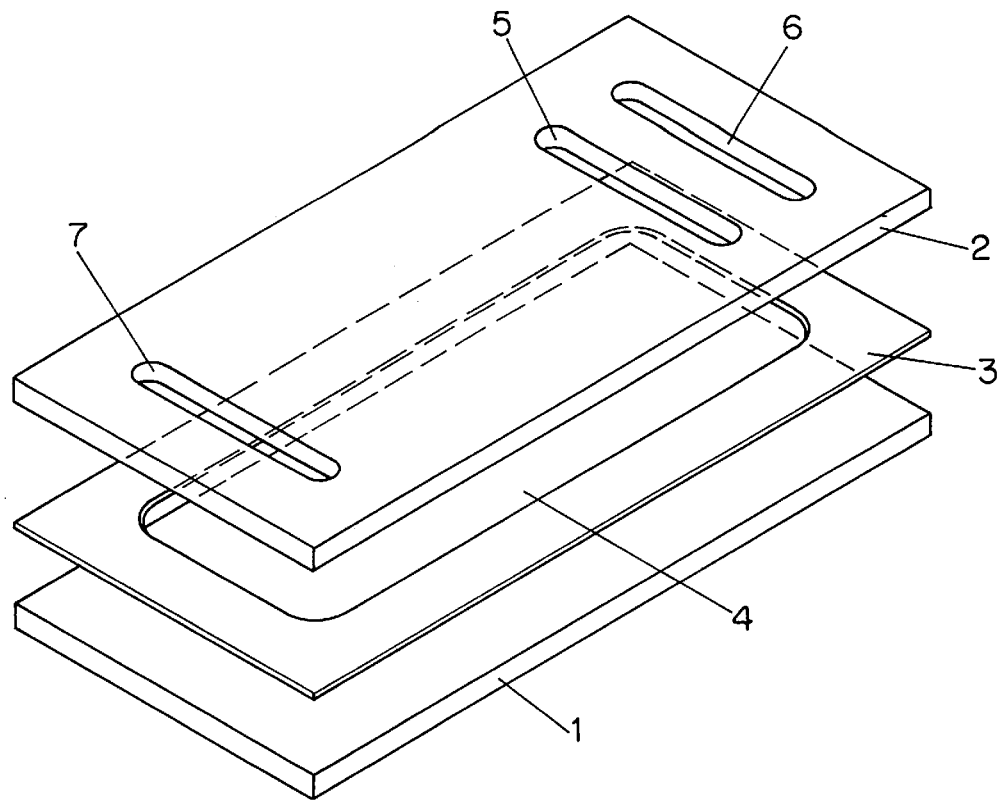
FIG. 1 shows an exploded view of a first embodiment of a microgel in accordance with the invention.

FIG. 1 shows an exploded view of a first embodiment of a microgel in accordance with the invention. As shown, the microgel is formed from a bottom substrate 1, a top substrate 2, and a spacer 3 sandwiched between the two substrates. The spacer 3 and the interior surfaces of the two substrates 1,2 define a gel compartment 4. Top substrate 2 has a slot 5 cut therein to permit loading of a sample onto the gel and slots 6 and 7 through which electrodes can be placed in contact with the gel.

The microgel shown in FIG. 1 can be made by a "squash-filling" process as follows. First, the spacer 3 is adhered to the bottom substrate 1. The area of the gel compartment 4 is then filled with unpolymerized or partially polymerized gel, and the top substrate 2 is pressed down over the top. The unpolymerized gel fills the gel compartment 4, with any excess gel being squeezed out between around the edges of the substrate. The gel is then polymerized, and the excess is trimmed off.

Figure 2:
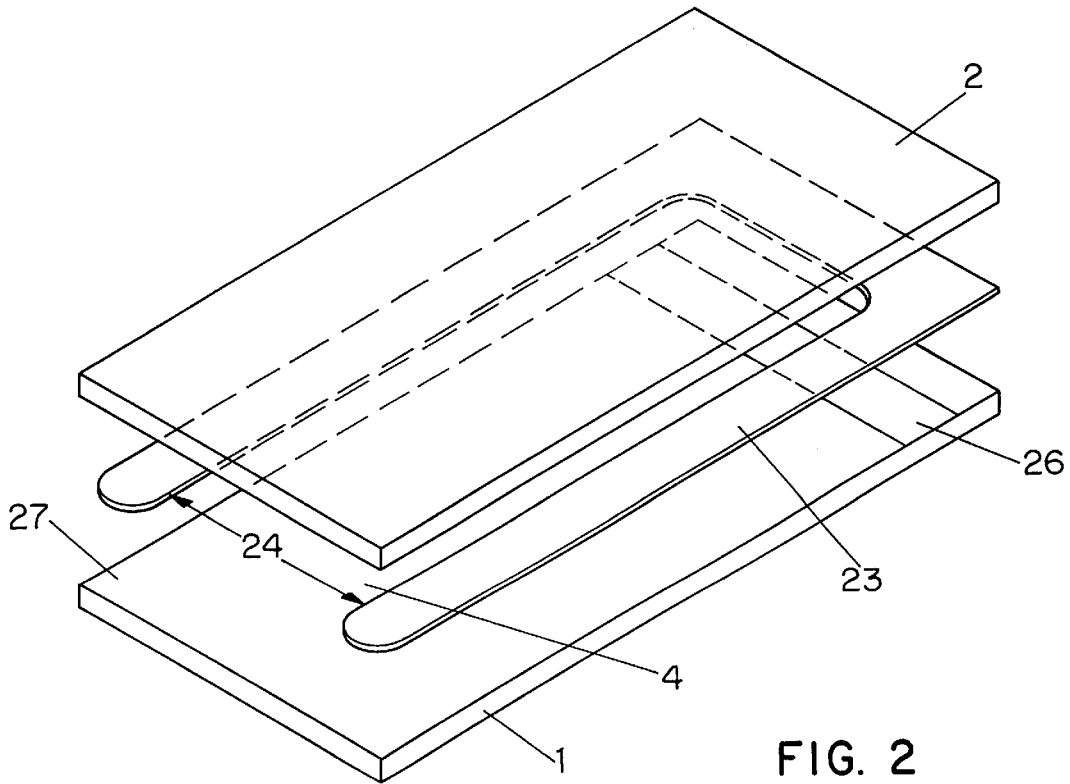
FIG. 2 shows a second embodiment of a microgel in accordance with the invention.

FIG. 2 shows an exploded view of a second embodiment of a microgel in accordance with the invention which is adapted to be filled by a different technique. In FIG. 2, the spacer 23 only extends along three sides of the bottom substrate 1, leaving an opening 24 along the fourth edge. As an alternative to the electrode slots 6 and 7 shown in FIG. 1, electrodes 26 and 27, may be deposited as a film directly on the top or bottom substrates. Suitable electrode materials are thin films of conductive materials such as indium tin oxide (ITO) or platinum. Solution buffered electrodes, i.e. electrodes in which the electrical contact between a conventional metallic (e.g. platinum) electrode and the gel is indirect, and is mediated by a concentrated electrolyte solution, may also be used.

A microgel of the type shown in FIG. 2 can be made by first adhering the bottom substrate 1, the spacer 23 and the top substrate 2 together to form a gel holder assembly. The gel holder assembly is then placed in a chamber and positioned vertically with the opening 24 directed downwards over a reservoir of unpolymerized gel. The chamber is then evacuated, the gel holder assembly is lowered to immerse the opening in the unpolymerized gel, and a gas is reintroduced into the chamber at positive pressure to drive the gel into the gel compartment 4 of the gel holder assembly. No slots are necessary in the top substrate of this embodiment, because the gel is exposed through the opening 24, permitting edge loading of the gel, although one or more slots in the top substrate may be provided if desired for introduction of sample or electrodes.

Figure 3:
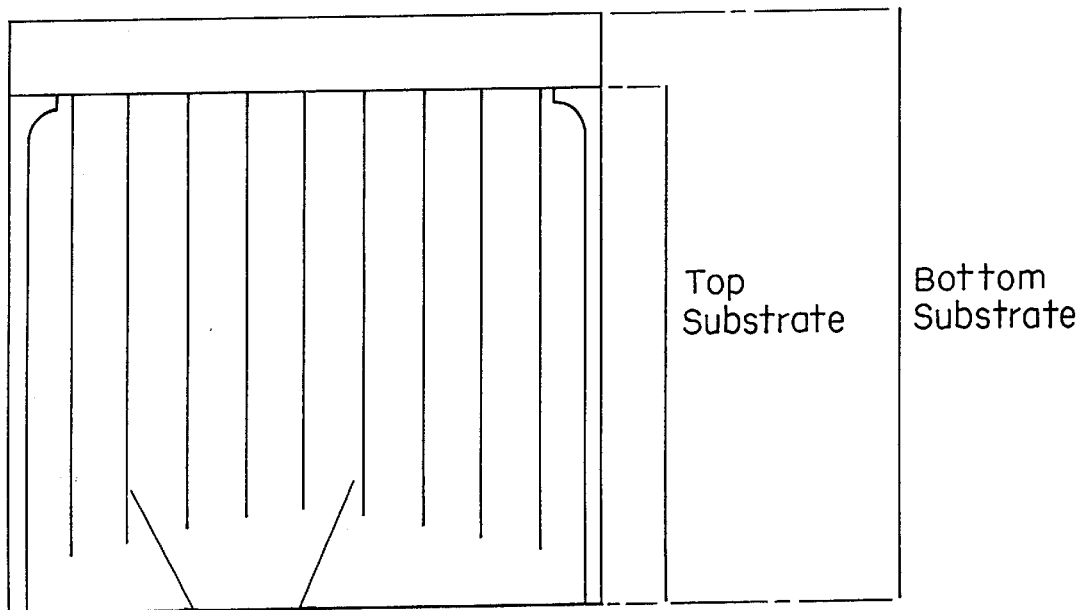
FIG. 3 shows a third embodiment of the invention.

A third embodiment of the invention is shown in FIG. 3. In this case, spacers have been used to create lane markers 30 within the body of the gel. Such lane markers may be incorporated to separate every lane, every fourth lane, or at such other interals as may be preferred by the user. In a preferred configuration employing lane separators the gel is separated into a number of lanes of equal width. The number of these lanes is determined by the formula (A/4), where A is the number of useable sample loading sites in the gel.

When the top substrate is shorter than the bottom substrate as shown in FIG. 3 it has been found to be advantageous to extend the lanes beyond the end of the top substrate across at least a part of the extending portion of the bottom substrate. This results in all lanes filling individually from the bottom up, and eliminates the possibility of unpolymerized gel from one lane spilling over into an adjacent lane and causing a bubble to form in the middle of that lane.

Figure 4A:
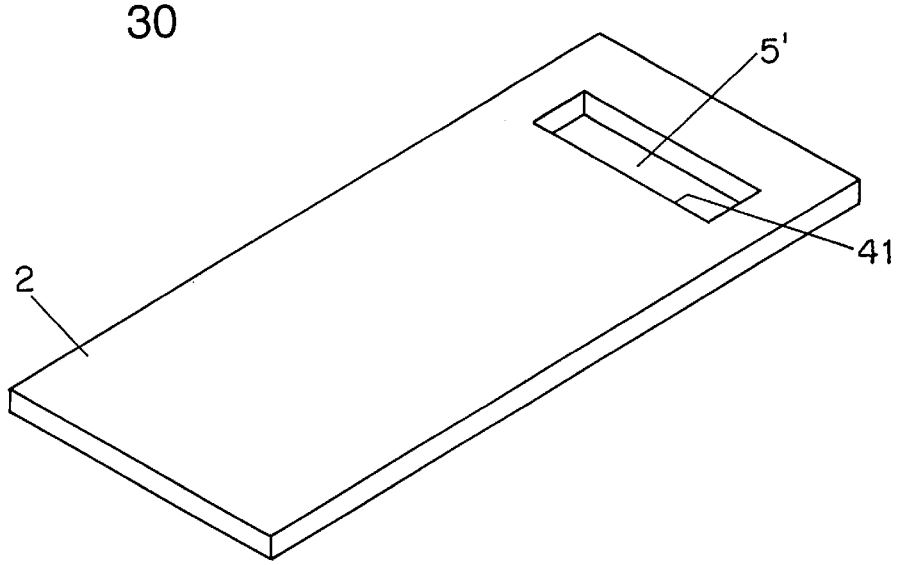
FIGS. 4A and 4B show a further embodiment of the invention.
Figure 4B:
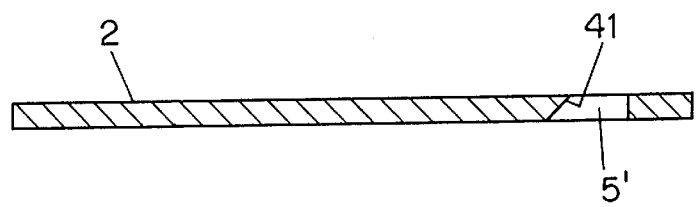

FIGS. 4A and 4B show a variation of a top substrate 2 with a window 5' cut therein to permit loading of sample. The edges of the window are all cut at 90°, except for the lower edge 31 which is cut with a 30° to 60°, preferably a 45° bevel, as shown most clearly in FIG. 4B. This design permits improved sample loading.

Figure 5A:
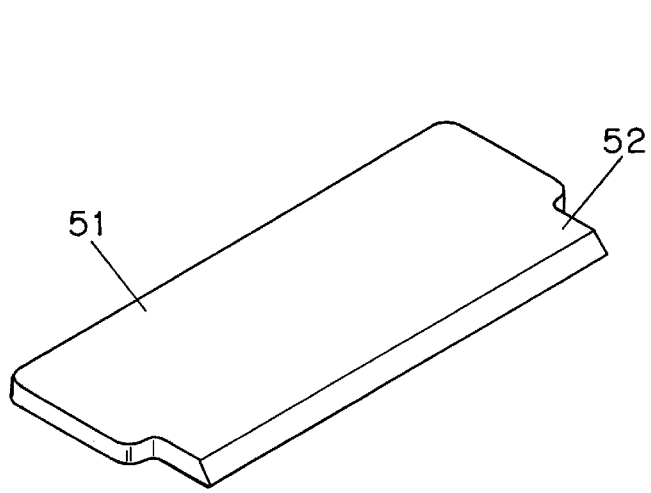
FIGS. 5A and 5B show a gel forming insert useful in practicing the claimed invention.

In particular, a microgel using a top substrate cut as shown in FIGS. 4A and 4B is preferably formed using a gel forming insert of the type shown in FIG. 5A. This insert has a base portion 1 and an insert portion 52. The insert portion 52 is notched at each end, such that it is narrower than the base portion. Preferably, the size of each notch is from 2–4 mm to 5 mm. The free edge of the insert portion is beveled to match the bevel formed in the lower edge 41 of the window 5', and the overall size of the insert is selected to permit insertion of the insert into the window 5'. For example, suitable dimensions are 12.5 cm wide, 1.5 cm in total height and 1 mm in thickness. A tab or handle may be placed on one surface of the base portion 41 to facilitate removal.

Figure 5B:
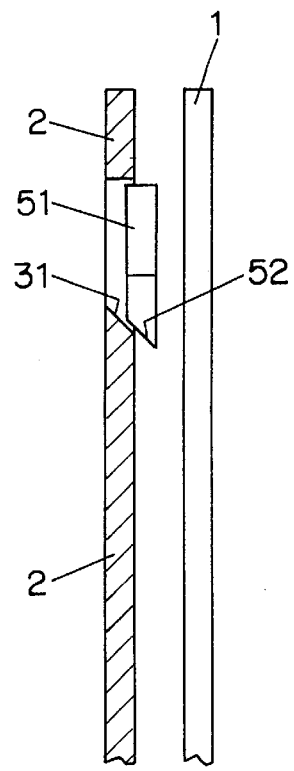

The gel forming insert is placed into the window as shown in FIG. 5B prior to the polymerization of the gel, preferably prior to the filling of the gel compartment. Adhesive tape may be used to constrain the movement of the gel forming insert so as to secure it against the bottom substrate and to prevent its floating on the injected solution. Upon injection of the proper amount of polymerizable solution into the microgel holder, the solution fills up the microgel compartment, up to the gel forming insert, where the solution flows partly around the edges of the gel forming insert, and it may bleed out of the microgel holder through the air holes. If there is a substantial excess of solution injected into the gel holder, the solution may even run out through the top. The excess gel is not of any significant consequence to the effective polymerization, sample loading, or use of the gel, and may be trimmed away if desired.

After UV catalyzed polymerization, it is important to the successful use of a microgel of the invention to delicately remove the gel forming insert without damaging the gel. After polymerization, if the gel holder is tilted into its facial plane, the gel forming insert will tend to fall forward. Gentle tapping on the bottom plate may be necessary to encourage the displacement of the gel forming insert. Once an edge of the gel forming insert has emerged from the plane of the top substrate, it may be grasped and gently pulled away from any polymerized gel which may be in contact with the gel forming insert. Alternatively, adhesive tape attached to the outside face of the gel forming insert may be used to pull the gel forming insert from its position. Either way, care should be taken to preserve the even edge of gel which will have formed along the bottom of the window of the top substrate.

Removal of the gel forming insert results in the formation of a trough running across the width of the gel bounded by the beveled edge of the window, the gel itself, and the bottom substrate into which the sample can be inserted. It is into this trough which sample is loaded for electrophoresis.

Figure 6:
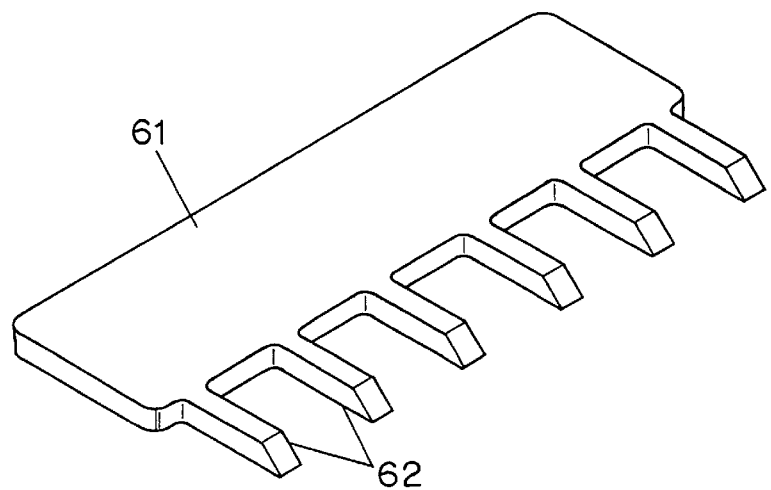
FIG. 6 shows a loading insert in accordance with the invention.

Because this trough is continuous across the width of the gel, it lacks the slots normally used in the loading of sample onto a gel. It is therefore desirable to use a specially adapted loading insert of the type shown in FIG. 6 when loading sample onto a gel formed as described above. The insert has a substantially rectangular base portion 61 having two long edges and two short edges; and a plurality of fingers 62 extending from one long edge of the base portion. Each of the fingers preferably has a width of from 0.5 to 3 mm. The fingers are evenly spaced at intervals of 2 to 7 mm in a region along the long edge of the base portion staring and ending at a point from 2 to 4 mm from the adjacent short edge of the base portion so that the fingers fit within the trough. The fingers further have a 30°–60° bevel at the distal end thereof to match the bevel of the loading insert and the lower edge of the window. This insert is placed into the trough formed by the gel forming insert, and sample is then loaded into the gaps between the fingers.

A second and alternative method of preparing and loading a microgel, requires forming the microgel in the presence of a polymerization comb insert which has a series of flattened extensions which will form wells for the loading of sample on the gel. The polymerization comb insert replaces the gel forming insert during the microgel filling and polymerization process. The dimensions of the polymerization comb insert are identical to the gel forming insert, except that instead of having a flat bottom edge beveled at a 45 degree angle to be complementary to the bottom edge of the window in the top substrate, a notch of about 2 mm width and about 5 mm depth is made at intervals, e.g, every 7 mm along the bottom edge. The result is a row of teeth, each tooth having a bottom edge beveled at 45 degrees to be complementary to the bottom edge of the window in the top substrate. Once placed in the open window of the microgel holder, the polymerization comb insert may be sealed in place with adhesive tape such that the entire window is completely covered. An opening for the air holes is then introduced into the adhesive tape. Solution is then injected into the microgel holder. The solution fills the microgel compartment and flows into the gaps in the teeth of the Polymerization Comb. Excess solution bleeds out of the air holes. The solution may then be polymerized with UV induced catalysis as described in the invention. When polymerization is complete, the adhesive tape and the polymerization comb insert are gently removed, leaving a row of gel columns vertically disposed against the bottom substrate. The gel columns act to define wells which can be used to separate samples loaded by the conventional methods. Microgels are found to have improved loading and using qualities if prior to the construction of the microgel holder, the gel compartment faces of the top substrate and bottom substrate are treated with Bind Silane (Pharmacia).

Figure 7A:
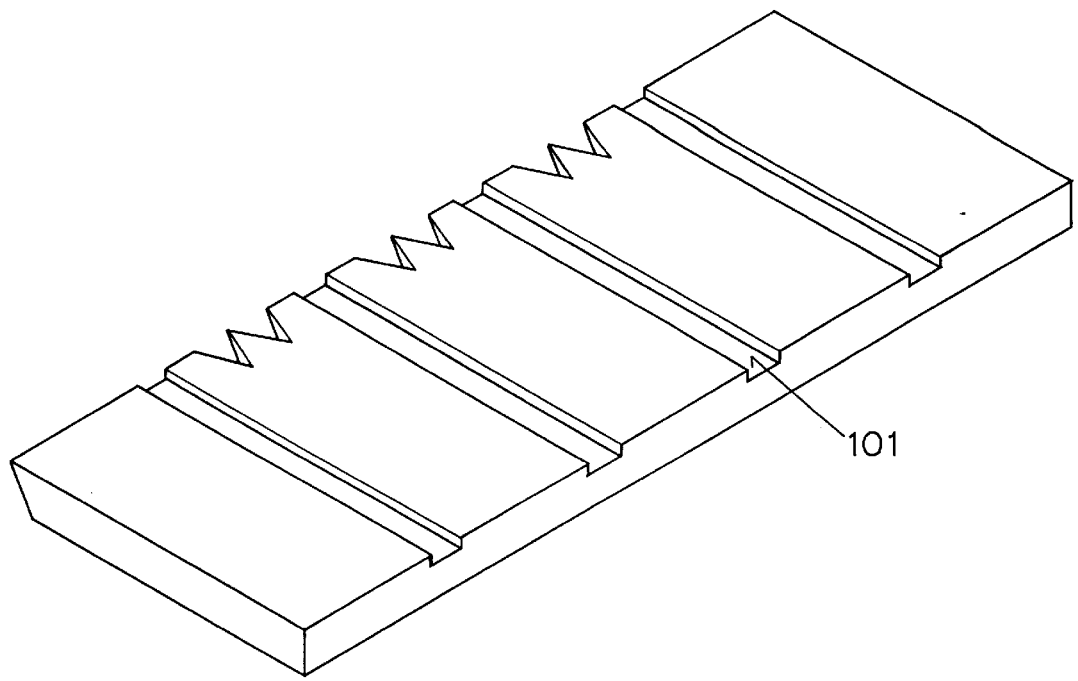
FIGS. 7A and 7B show further embodiments of loading and gel forming inserts in accordance with the invention.
Figure 7B:
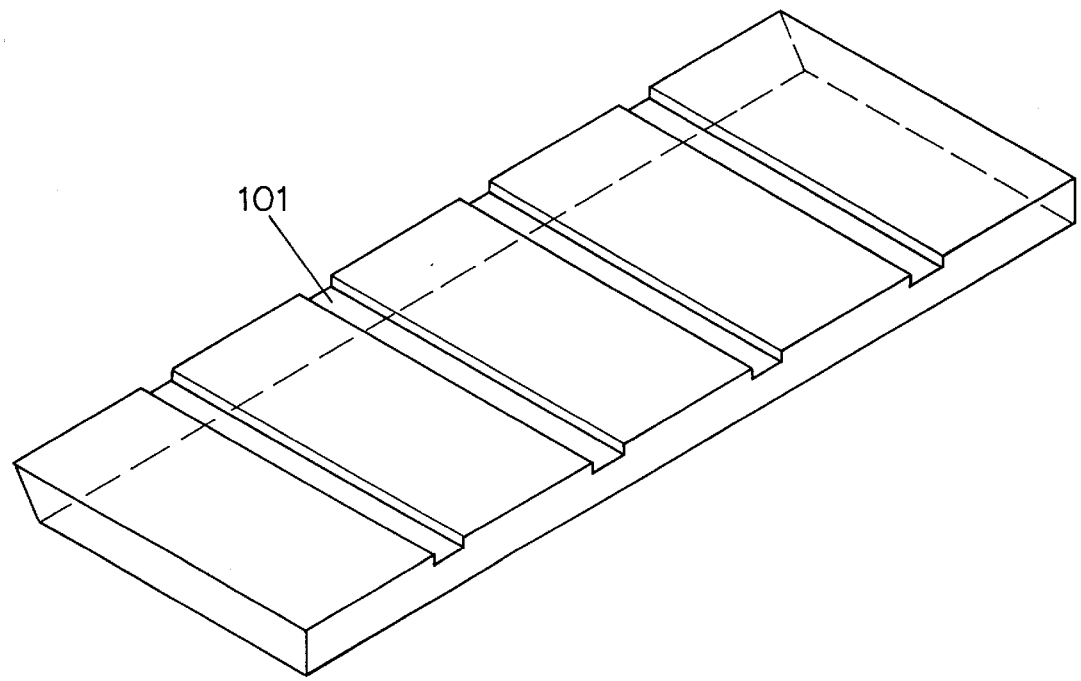

FIGS. 7A and 7B shows alternative designs for filling plug and loading combs useful when the lane dividers are present on the extended portion of the bottom substrate (FIG. 3). In this case, grooves 101 are formed along one surface of the inserts to accommodate the lane dividers. Advantageously, the grooves are slightly wider than the lane dividers to allow for air and excess gel to escape during the filling process.

The top and bottom substrates of the microgels of the invention are preferably transparent sheets of glass. For example 1 mm thick low-fluorescing glass is a preferred material for use as the top and bottom substrate of the invention. 1 mm Borosilicate glass which has greater ultraviolet light transparency is another preferred material. Other materials such as plastics may also be used, however, provided they do not fluoresce strongly in a region which would interfere with the detection of a luminescent label on the nucleic acid polymer being sequenced or inhibit the polymerization of the gel.

The spacers 3 in the microgels of the invention serve to create a gap between the top and bottom substrates to establish the gel compartment. In accordance with the invention, spacers are preferably selected such that this gap is between about 25 and 250 $\mu$m more preferably 25 to 100 $\mu$m. Smaller gaps are not really practical because of the greater care must be taken during fabrication, for example the use of clean room procedures to prevent dust particles which may be large relative to the desired gap from contaminating the surface of the substrate. Also, the extent to which both substrates are flat becomes more important as gap size decrease. Lastly, the amount of sample loaded onto the gel may need to be reduced to avoid loss of the gels resolving ability which means that there will be a smaller emitted signal from the sample to detect. Gaps larger than 250 mm can be used, but may be less desirable because the electrical resistance of a gel of any given composition increases as the gap size increases. This means that larger currents and hence greater resistive heating of the gel will occur for a given electric field strength in a thicker gel. Also, where the spacer is formed by applying adhesive to one or both substrates, it is necessary to build up an adhesive layer that is essentially the same thickness as the gap. It may be difficult to find an adhesive which is viscous enough to bridge the openings between spacers particles, has minimal flow out, permits settling of the substrate onto the spacers and minimizes voids formed in the application process.

One form of spacer useful in the invention is a polymeric film that is affixed to the top or bottom substrate with an adhesive. For example, vinyl films coated with an acrylate adhesive can be cut to the desired size and pattern to form spacers. Suitable vinyl films include 1, 2 and 4 mil films sold by 3M under the tradename SCOTCHCAL.

Spacers can also be formed by screen printing a slurry of particles in a hardenable material in the desired pattern onto the top or bottom substrate. For example, a UV-curable and/or thermally-curable acrylate adhesive slurried with graded silica particles of the appropriate size to define the desired gap between the substrates is a preferred material for use in forming a spacer by this mechanism. Suitable adhesives include Loctite CHIPBONDER™# 346, 347, 360 and 3603, IMPRUV™ 349, 363, 365 and 366 and General Purpose Ultraviolet Adhesive 352; and Minico® M07950-R acrylate adhesive.

An alternative to the use of an adhesive is to form a mixture from powdered low melting glass and solid particles of an appropriate size to form the spacer. This mixture is screen printed onto the substrate in the desired pattern, for example to form lanes within the gel compartment, and then heated to melt the powdered low melting glass. Upon cooling, the low melting glass resolidifies, bonding the solid particles to the substrate. In addition, the low-melting glass may be used alone or in conjunction with an adhesive to bond the top and the bottom substrates together.

The glass powder or "frit" will advantageously have a melting temperature of about 400° to 500° C., while the melting temperatures of the solid particles beads and the substrates will be form 600° to 800° C. Notwithstanding this difference in melting temperature, care should be taken to match the thermal expansion coefficients of the glass powder, substrates and solid particles to avoid fractures or voids due to shrinkage on cooling. Acceptable results are achieved when the thermal expansion coefficients of the materials are within about 10% of each other.

Dispersions of particles in an adhesive can also be applied using a robotic glue gun which paints the adhesive onto the glass substrate in the desired pattern. This has the advantage over screen printing that nothing actually touches the substrate other than the adhesive.

Spacers can be formed using this approach on a single substrate. It is preferred, however, to print matching patterns on both the top and bottom substrate that are aligned and pressed together to form the spacer between the two substrates. While this method introduces the need for careful alignment, it has been found that it has the advantage of reducing the formation of bubbles and voids in the spacer lines, thus leading to a more consistent product.

The spacing between the two substrates may be further defined and maintained by a dispersion of solid beads within the gels itself. This can be achieved by evenly spreading a slurry of beads, for example glass beads of the appropriate size in a volatile solvent onto the interior surface of one of the substrates prior to the formation of the gel holder. The solvent is evaporated off, leaving the solid particles distributed on the surface of the substrate.

The gels of the invention offer the further advantage of high consistency from one gel to the next. This advantages is principally derived from the use of carefully controlled spacer thicknesses in a mass production approach.

Microgels in accordance of the invention can be used to analyze quickly and accurately a mixture of fluorescently-labeled oligonucleotide fragments of differing lengths. Basically, this process involves first loading the mixture onto an origination site on a microgel in accordance with the invention, and applying a potential to the electrophoresis gel whereby a current flows through the electrophoresis gel and transports the oligonucleotide fragments in the mixture away from the origination site and through a monitoring site remote from the origination site on the gel. Fluorescent emission from oligonucleotides passing the monitoring point is then detected.

As noted above electrode configurations for applying the potential to the gel may be of several types. Through these electrodes, a field of up to 350 V/cm, preferably 150–350 V/cm, is applied using a standard electrophoresis power supply. This high field strength offers the advantages of rapid migration of the fragments through the gel, resulting in a reduced time to analyze the fragments. The rapid migration also reduces the impact of diffusion of fragments in the gel, which yields better resolution. Field strengths of this magnitude are not practically useful in a macrogel, i.e., a gel having a thickness of 0.35 mm (350 mm) or greater, because of the enormous current flow and resultant heating that would occur.

Figure 8:
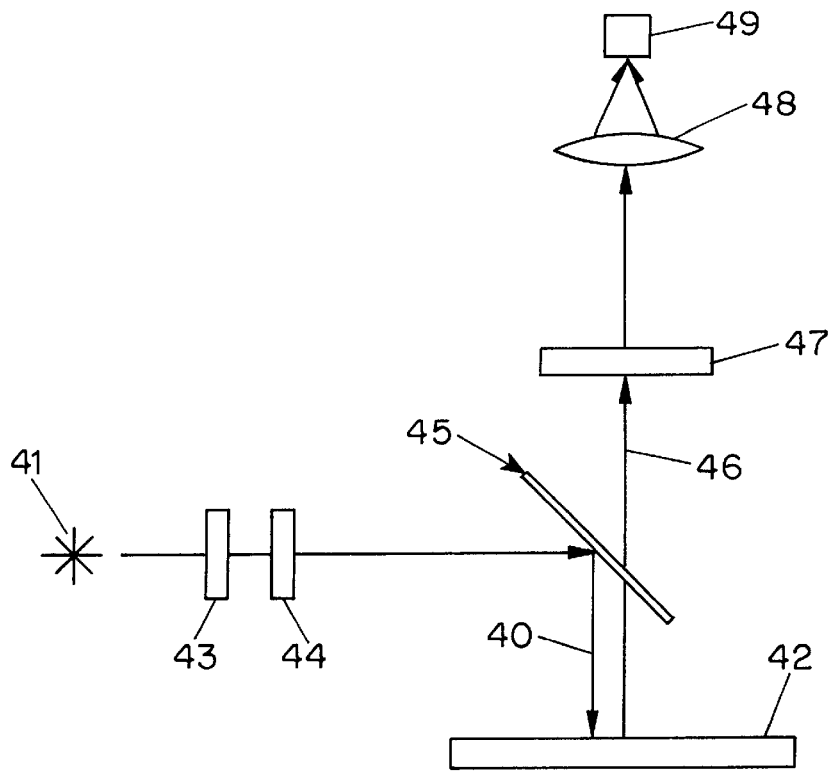
FIG. 8 shows an apparatus for use in analyzing oligonucleotide mixtures in accordance with the invention.

FIG. 8 shows one apparatus for use in analyzing oligonucleotide mixtures. In FIG. 8, a light source 41, such as an argon ion laser, shines an excitation beam 40 approximately parallel to the surface of the microgel 42. The excitation beam passes through a beam expander 43 and an interference filter 44 that removes undesired wavelengths of light, and then strikes a diffracting mirror 45 selected to reflect light of the excitation wavelength and transmit light of the wavelength at which the fluorescent marker emits. The diffracting mirror 45 reflects the excitation beam 40 onto the microgel 42. When fluorescently labeled oligonucleotides pass through the beam, light is emitted in all directions, including back towards the diffracting mirror 45. This light 46 passes through the diffracting mirror 45, an interference filter 47 selected to isolate the emission wavelength from scatter and non-specific fluorescence, and a lens 48 that focuses the beam 46 on a photomultiplier tube 49.

Figure 9:
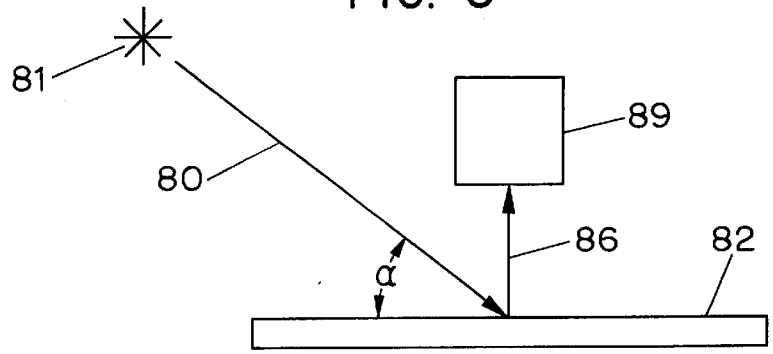
FIG. 9 shows an apparatus for use in analyzing oligonucleotide mixtures in accordance with the invention.

FIG. 9 shows an alternative apparatus for analyzing oligonucleotide mixtures in accordance with the invention. As shown, excitation beam 80 from light source 81 strikes the surface of the microgel 82 at an angle a, generally from 45 to 65 degrees. Light 86 emitted in the direction of a photomultiplier tube 89, optionally passing through collection lenses and filters (not shown).

Other apparatus and apparatus configurations may also be used. For example, while the apparatus shown in both FIGS. 8 and 9 use photomultiplier tubes as the detector, other types of detectors such as photodiodes may also be employed. Photodiodes may be particularly useful in an apparatus using an array of detectors aligned with the expected tracks of a plurality of samples on a single gel.

Furthermore, it will be understood by persons skilled in the art that the invention is not limited to the use of argon ion lasers as the light source. While the argon ion laser is convenient because its emission at 488 nm is effective to excite fluorescein, the use of other labels, with different absorption maxima may argue for the use of other type of lasers, or for the use of conventional light sources such as mercury or xenon lamps, combined with appropriate filters.

The microgel holders of the present invention may in principle be used to form microgels using any type of gel forming material, including agarose gels. The preferred gel material, however, is a polyacrylamide gel. Polyacrylamide microgels in accordance with the invention, may be formed using either a chemical cross-linking agent catalyst such as TEMED and ammonium persulfate or a photoactivated cross-linking system such as riboflavin and ultraviolet light, or methylene blue and blue (450 nm) light.

Where photopolymerized gels are used in combination with a photocurable adhesive, it may be advantageous to select the gel and adhesive such that the polymerization wavelengths for the two systems are different. This flows from the observation that some UV-activated adhesives contain materials which quench the subsequent curing of UV-cured gels, either through absorption of the exciting light or by quenching the excited states of the gel polymerization initiator. By shifting the gel polymerization to a different wavelength, this quenching effect is reduced or eliminated.

Prior to the use of a gel for analysis of oligonucleotide fragments, it may be desirable to pre-run the gel, i.e. to apply a potential gradient with running buffer, but without the application of a sample. Such a pre-run may remove excess reactants from the polymerization reaction which could interfere with migration or detection of the oligonucleotides. In addition, since some constituents used in the running buffer, notably urea, may tend to degrade acrylamide gels, the shelf life of the microgel can be improved by introducing these components just before the actual running of the analysis.

The use of the invention will now be further illustrated through the following non-limiting examples.

EXAMPLE 1

Gels were prepared using 6% acrylamide (19:1 acrylamide:bis-acrylamide, 7M urea, 0.6×TBE) in gel holders formed from 1 mm thick calendared glass. The bottom plate had a 50 mm gasket surrounding the edge of the plate and forming a central opening 15 mm wide and 75 mm long. Unpolymerized gel was placed in the opening and the top plate placed over it to squash the gel to its desired 50 mm thickness as defined by the gasket spacer. After polymerization, excess gel was trimmed from around the edges of the glass plate.

A test sample was prepared containing a mixture of 0.1 ng/ml of a 30-mer having the sequence ATCGGCTAAT CGGCTAATCG GCTAATCGGC [Seq ID No.: 1]

and 0.1 ng/ml of a 31-mer having the sequence

ATCGGCTAAT CGGCTAATCG GCTAATCGGC T [Seq ID No. 2].

These oligonucleotides were synthesized by a commercial supplier of custom oligonucleotides (Oligos Etc.) in accordance with the inventors' instructions, and were labeled with fluorescein at the 5'-end.

Figure 10:
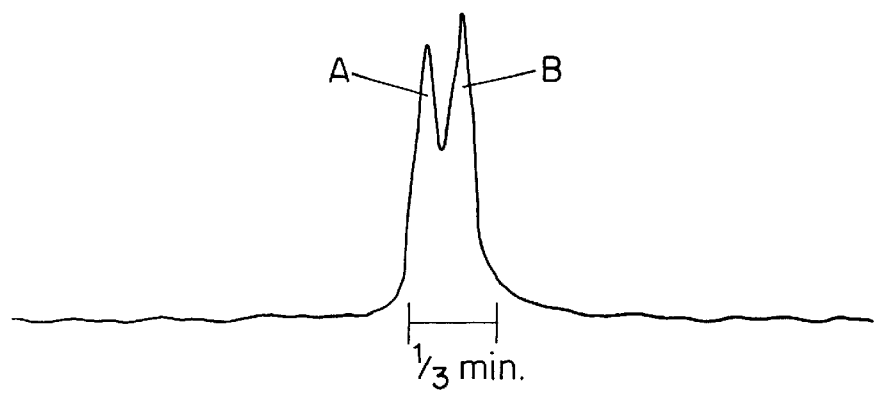
FIG. 10 shows the results of an analysis of a mixture of a 30-mer and a 31-mer using the present invention.
Figure 11A:
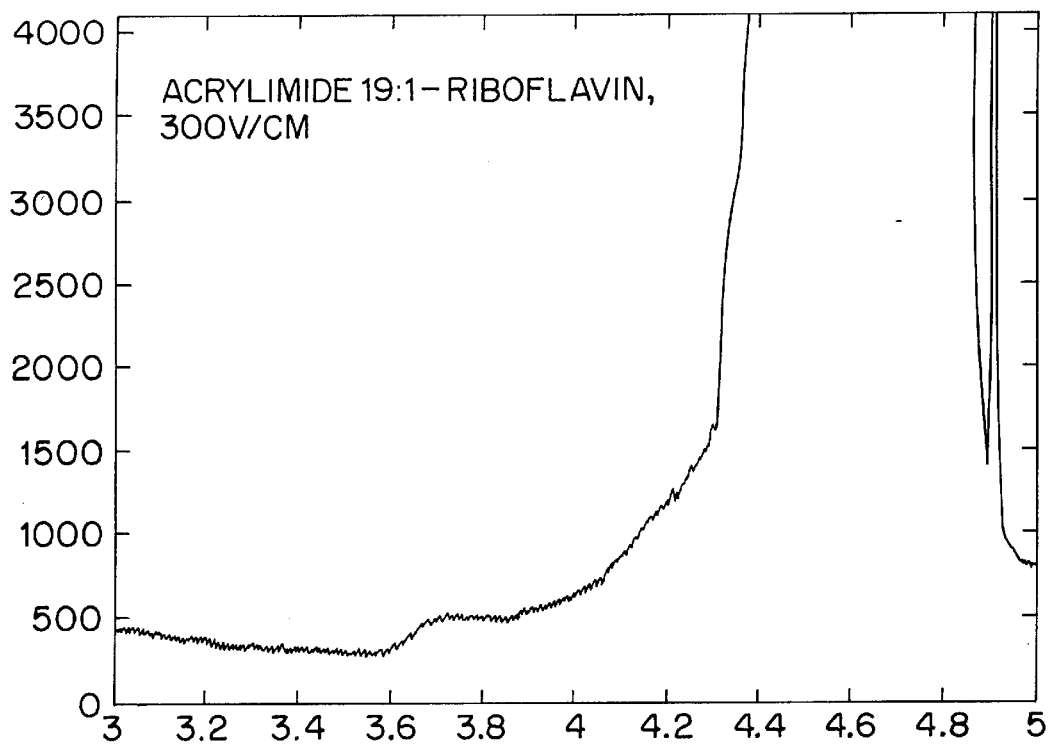
FIGS. 11A–11F show the results of an analysis of the ddT sequencing reactions of M13 DNA template.
Figure 11B:
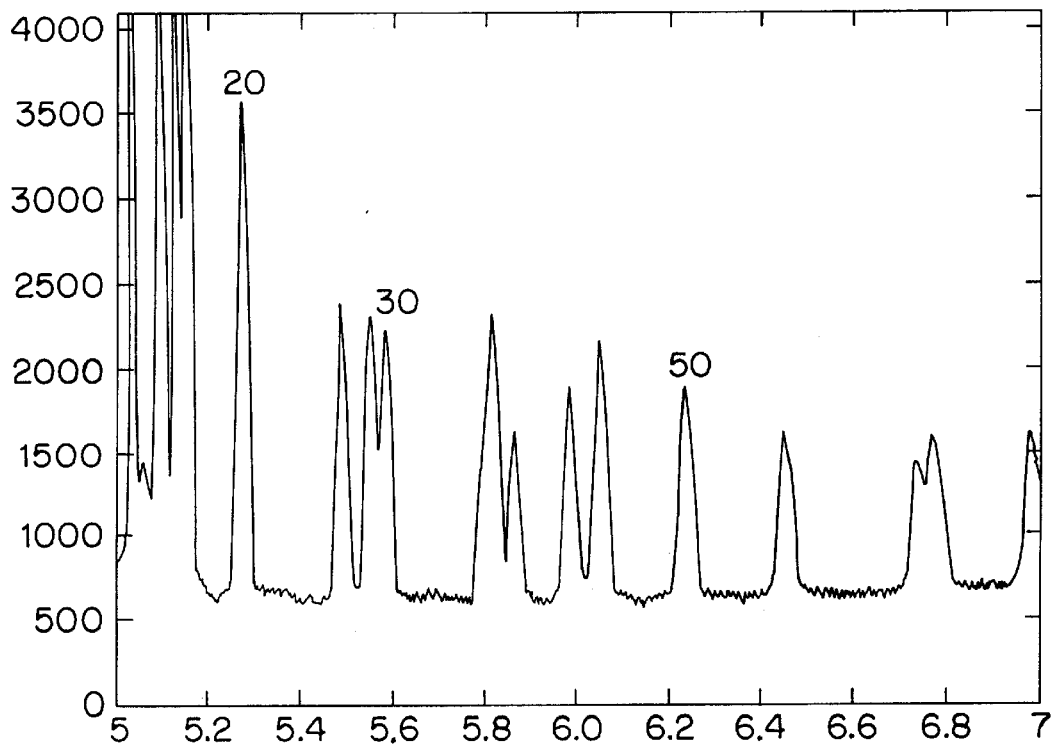
Figure 11C:
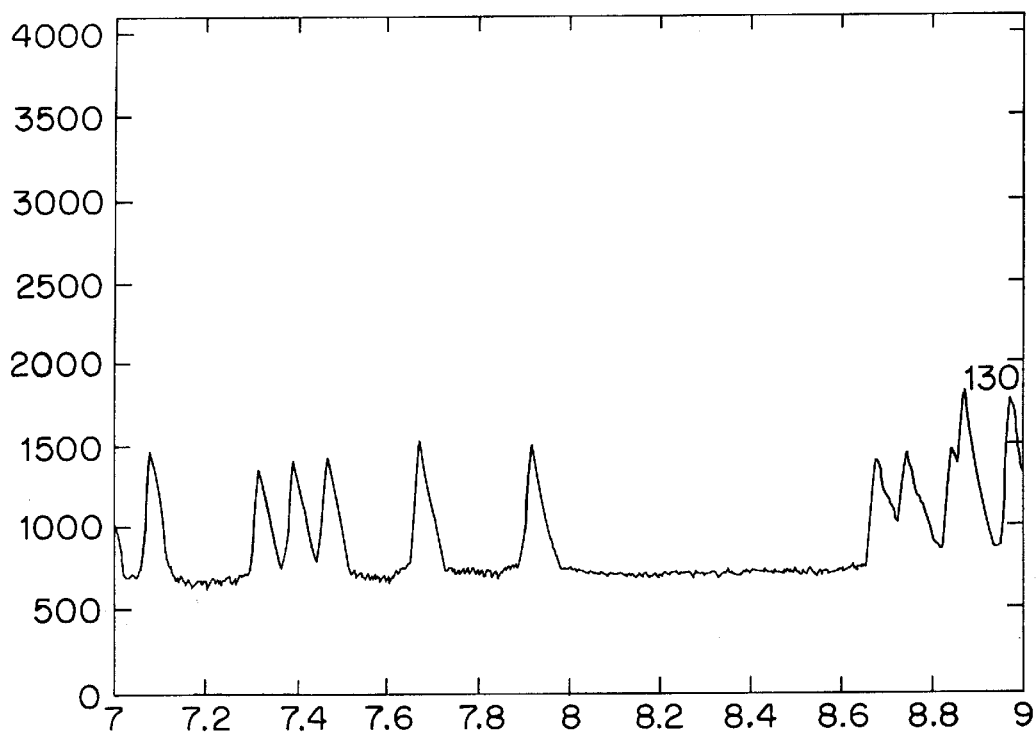
Figure 11D:
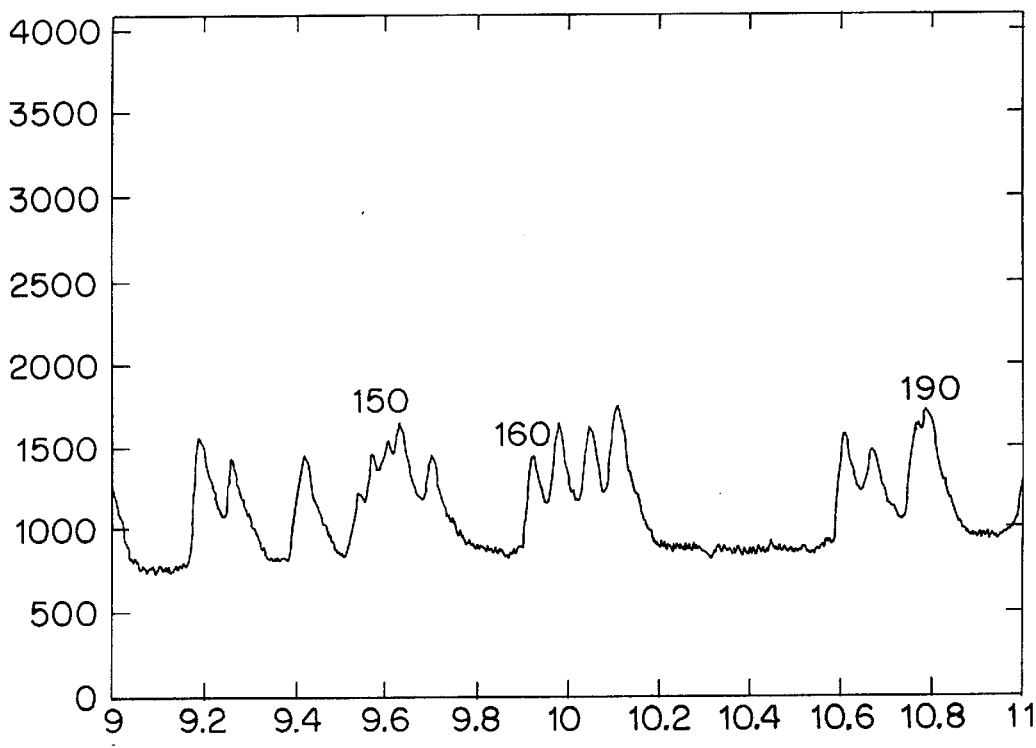
Figure 11E:
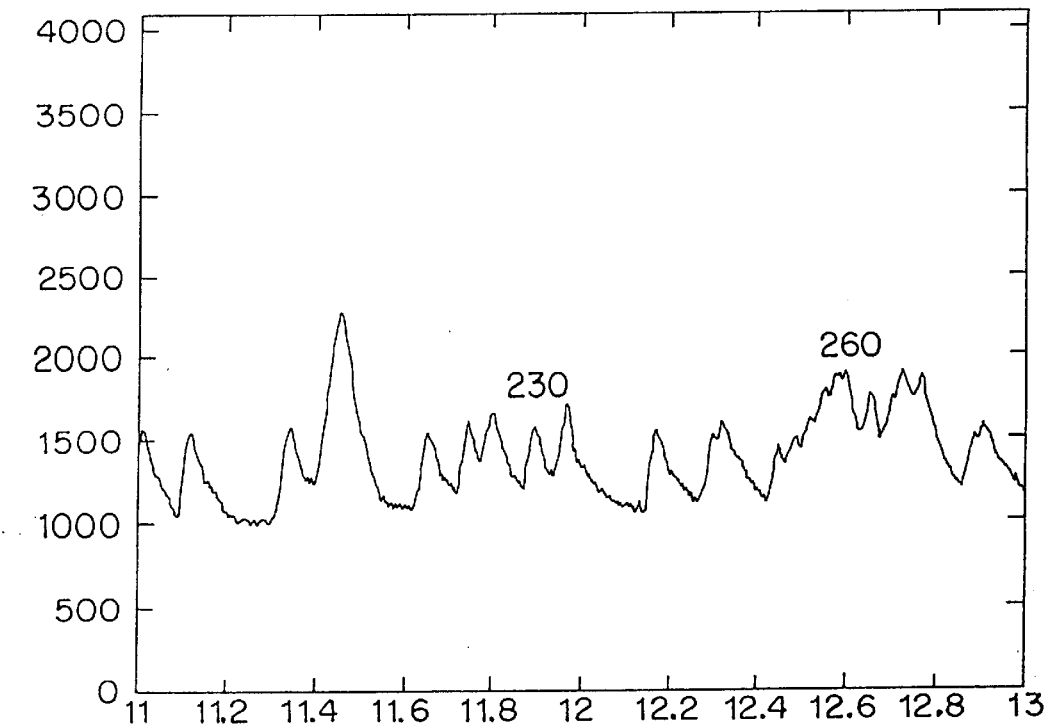
Figure 11F:
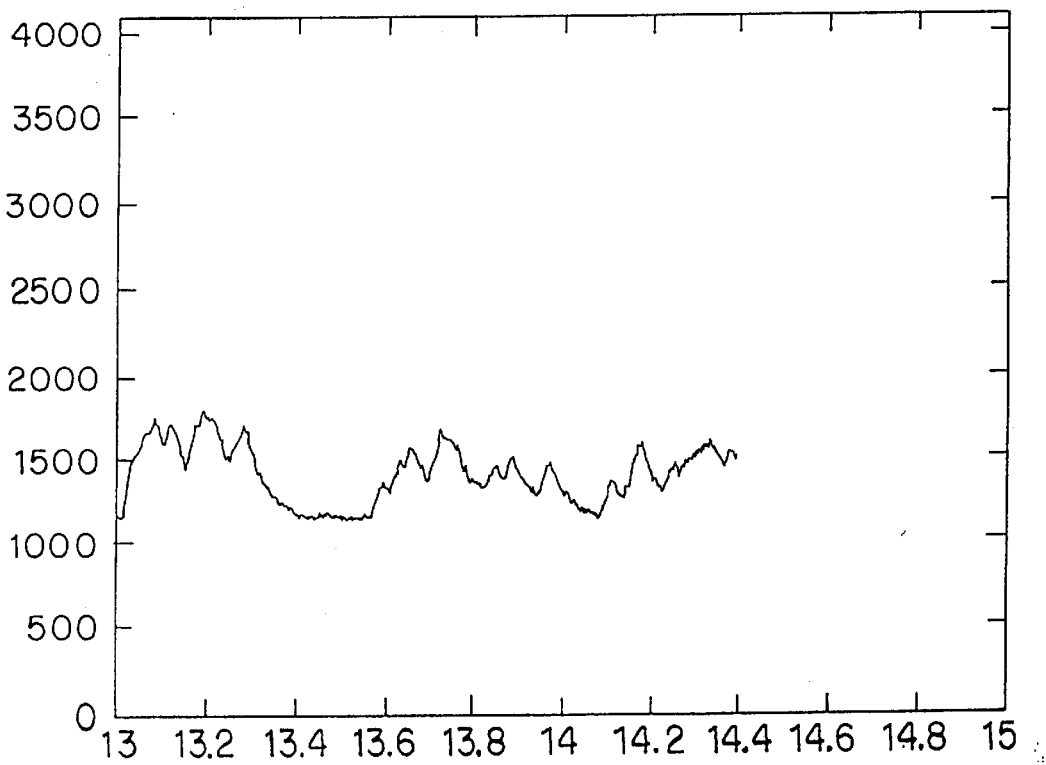

100 nl of the test sample (containing~100 femtomoles of each oligonucleotide) was edge loaded onto the top of the gel using a capillary. A field of 100 V/cm was then applied to the gel by laying an electrode consisting of a 0.25 mm thick strip of indium tin oxide, 35 mm×8 mm in size, across each end of the polymerized gel, then connecting the electrodes to an electrophoresis power supply. An argon ion laser detection system of the type shown in FIG. 8 was used to detect passage of the fluorescein-labeled oligonucleotides past a point located 55–65 mm from the origin. The signal detected by the photomultiplier tube is shown in FIG. 10. The signal was resolved into two peaks corresponding to the 30-mer (peak A) and the 31-mer (peak B) within a run time of 3 minutes.

EXAMPLE 2

A UV activated adhesive matrix was prepared using Minico® M07950-R acrylate adhesive from Emerson & Cuming Inc., Woburn, Mass., mixed with 2% by weight Sigma® glass beads (106 micron and finer) filtered to select beads of a size of 45 to 53 microns. The adhesive matrix was screen printed onto the bottom substrate in the pattern shown in FIG. 3. The top substrate was then positioned on top of the bottom substrate as illustrated in FIG. 3. The substrates were then exposed to 20 Watts UVA light (wavelength 315–385 nm) to initiate curing of the adhesive and to bond the two substrates together.

After the adhesive was cured, the gel holder was placed horizontally in a rectangular filling device of the type described in U.S. patent application Ser. No. 08/332,892 and the con-currently filed CIP thereof, which are incorporated herein by reference. Briefly, the microgel holder was laid horizontally in a quadrilateral filling frame, and placed on the upper shelf within a filling cabinet. In the cabinet, a polyacrylamide gel forming solution was driven into the gel holder, which was then exposed to ultraviolet light from 20 W UVA-lamps disposed on the interior of the filling cabinet for a period of time sufficient to polymerize the gel.

The gel forming solution used contained 6% acrylamide (19:1 bis-acrylamide), 7M urea in 0.6×TBE and 10 ppm riboflavin. The riboflavin was introduced by adding 10 µl of a 0.4% aqueous riboflavin solution to 25 ml of acrylamide solution.

EXAMPLE 3

A UV activated adhesive matrix of the type described in Example 2 was screen printed onto the bottom substrate in the pattern shown in FIG. 2. One ml of a slurry of 100% ethanol and 1% by weight glass beads (45 to 53 microns) was applied to and evenly distri-buted across the bottom substrate. After five minutes at room temperature, the top substrate was positioned over the bottom substrate as illustrated in FIG. 2, and the substrates were pressed together. The substrates were then exposed to 20 Watts UV lights (315–385 nm) to initiate curing if the adhesive, and to bond the two substrates together to form a gel holder.

Acrylamide solution was injected into the microgel holder and polymerized as described in Example 2. The force of the injection washed out a portion of the smallest sized glass beads. These beads were easily removed from the top of the gel prior to insertion of the Loading Insert.

EXAMPLE 4

A microgel was prepared as in EXAMPLE 2, using the Insert Panel during the polymerization of the microgel. The Insert Panel was carefully removed and replaced by the Loading Insert. The microgel holder was mounted vertically in an electrophoresis apparatus. 3 µl of a prepared solution containing the products of a completed fluorescein-labeled ddT DNA sequencing reaction of M13 template DNA, with methylene blue and xylenc cyanol as additional visible separation markers, was pipetted into a loading well.

A TBE solution electrode was formed by gasket sealing the microgel window against a TBE reservoir containing a platinum electrode. The "bottom" of the microgel was immersed in a TBE reservoir containing a platinum electrode. The back of the microgel holder was secured against an alumina plate by vacuum suction in order to dissipate heat during the electrophoresis. An electric potential was applied between the two electrodes, generating an electric field of 300 V/cm through the microgel.

Under the clectromotive force, DNA fragments migrated through the microgel and through the detection zone. An argon ion laser detection system of the type shown in FIG. 8 was used to detect passage of the fluorescein-labeled fragments past a point located 100 mm from the origin. The signal detected from the ddT reactions by the photomultiplier tube as a function of time is shown in FIGS. 11A–11F. As may be seen in FIGS. 11A–11F. ddT extension products of 1 nucleotide beyond the primer are observed about 4.9 minutes after the start of electrophoresis. Fragments of at least 300 nucleotides may be clearly resolved within 13.8 minutes from the start electrophoresis.

EXAMPLE 5

A microgel is formed as in Example 2 except that a methylene blue initiator system is used in place of riboflavin. This initiator system consists of 100 µM methylene blue, 1 mM sodium toluene sulfinate and 50 µM diphenyliodonium chloride. The gel is polymerized using a source of blue (450 nm) light such as a quartz-halogen lamp.

EXAMPLE 6

A screen printable low-melting glass composition is prepared by combining Glass No. 7570 obtained from Ferro Corporation (Cleveland. Ohio) with a binder identified as Product 80 863 and sold by Cerdec Corporation (Frankfurt. Germany) in a ration of 10:3 or 1:1, and 1 to 10% by weight of solid particles in the form of glass beads prepared as in Example 2 above. Glass No. 7570 has a particles size, $D_{50}$ of 30.99 microns, a thermal expansion coefficient (25°–260° C.) if $82.6 \times 10^{-7}/°C.$, a density of 5.36 g/cm$^3$, and a softening point of 449° C. Product 80 683 is a water soluble binder used conventionally for application of glazes to porcelain or ceramics. Other products which might be used in this capacity include METHOCEL binders available from Dow Chemical.

After mixing the three components of the paste together, the paste is screen printed onto one glass substrate plate in the desired pattern, for example the patterns shown in FIG. 2 or FIG. 3. The substrate is then heated to 125° C. for 10 minutes and 320° C. for 10 minutes to prepare the paste for sealing. For sealing, the plate is put in a furnace at 450° C. for 25 minutes to pre-fuse the glass powder. A second substrate plate is then placed on top of the first plate with the pre-fused material sandwiched in between. The whole assembly is then placed in a furnace at 470° C. for another 25 minutes, causing final binding of the plates together. In order to ensure evenness of the gap between the plates, pressure is applied to the outside faces of the plates. This pressure may be generated by clamping, by placing a weight onto the uppermost substrate or using an air driven piston directed from the top, downwards against the substrates.

What is claimed is:

1. A method for making an electrophoresis gel, comprising the steps of:
    (a) applying a plurality of solid particles to a surface of a first substrate;
    (b) forming a gel holder comprising the first substrate, and a second substrate by partially sealing the first substrate to the second substrate such that the plurality of solid particles is disposed between the first and second substrate, and such that a gel compartment having a thickness 250 microns or less is formed between the first substrate and the second substrate, said gel compartment having an opening for the introduction of gel;
    (c) filling the gel compartment with an unpolymerized gel; and
    (d) polymerizing the gel in the gel compartment, wherein the solid particles have a size substantially equal to the thickness of the gel compartment.

2. A method according to claim 1, wherein the solid particles are applied to the substrate as a mixture with a powdered, low-melting glass further comprising the steps of
    heating the substrate having the solid particles and the powdered, low-melting glass thereon to melt the low-melting glass, and
    cooling the heated substrate to resolidify the low melting glass, whereby the solid particles are bonded to the surface of the substrate by the resolidified glass.

3. A method according to claim 1, wherein the first substrate is sealed to the second substrate with an adhesive.

4. A method according to claim 3, wherein the adhesive is applied by screen printing.

5. A method according to claim 3, wherein at least a portion of the solid particles are dispersed within the adhesive.

6. A method according to claim 5, wherein the adhesive is an acrylate adhesive.

7. A method according to claim 1, wherein the separation between the substrates is from 25 to 100 microns.

8. A method according to claim 1, wherein the gel is polyacrylamide.

9. A method according to claim 1, wherein the gel is separated into two or more lanes.

10. A method according to claim 9, wherein the lanes are separated by lines of adhesive containing at least a portion of the solid particles.

11. A method according to claim 1, wherein at least a portion of the solid particles are disposed on a surface of the top substrate or the bottom substrate prior to the formation of the gel compartment, whereby the plurality of particles are disposed within the gel compartment of the microgel.

12. A method according to claim 11, wherein the solid particles are disposed on the top substrate or the bottom substrate by application of a slurry of particles in a volatile liquid which is evaporated prior to the formation of the gel compartment.

13. A method according to claim 1, wherein the gel is photopolymerized.

14. A method according to claim 1, further comprising the step of cutting sample introduction and electrode holes in the top substrate prior to its assembly into the gel holder.

15. A method according to claim 14, wherein the sample introduction and electrode holes are sealed over by a removable adhesive strip prior to the filling of the gel compartment.

16. A method according to claim 15, wherein the removable adhesive strip permits transmission of UV light.

17. A method according to claim 11, further comprising the step of cutting a substantially rectangular sample introduction hole into the top substrate prior to its assembly into a gel holder, said sample introduction hole being formed near a first end top substrate such that sample loaded through the sample introduction hole will migrate towards a second, opposite end of the top substrate.

18. A method according to claim 17, wherein the sample introduction hole has a long edge closest to the second end of the substrate, and said long edge is beveled such that the sample introduction hole has larger dimensions on a first surface than on an opposite second surface, and wherein the gel holder is assembled such that the first surface is on the inside of the gel holder.

19. A method according to claim 18, further comprising the step of placing an insert into the sample introduction hole prior to polymerization of the gel, wherein the insert is beveled to match the bevel of the sample introduction hole such that a trough is formed between the beveled edge of the top substrate and the gel into which sample may be loaded.

20. A method for analyzing a mixture of labeled oligonucleotide fragments of different lengths comprising:
  (a) loading the mixture onto an origination site on a microgel,
  (b) applying a potential to the electrophoresis gel creating an electric field strength of 100 V/cm or greater, whereby a current flows through the electrophoresis gel and transports the oligonucleotide fragments in the mixture away from the origination site and through a monitoring site remote from the origination site on the gel; and
  (c) detecting oligonucleotides passing the monitoring point, wherein the microgel comprises
    a top substrate and a bottom substrate sealed to one another to form a gel compartment having a thickness of from 250 microns or less,
    a plurality of solid particles having a mean diameter substantially equal to the thickness of the gel compartment, said plurality of solid particles being disposed within the gel compartment, and
    an electrophoresis gel disposed within the gel compartment.

21. A method according to claim 20, wherein the electrophoresis gel is polyacrylamide.

22. A method according to claim 20, wherein at least a portion of the solid particles are dispersed in an adhesive which seals the top substrate to the bottom substrate.

23. A method according to claim 22, wherein the adhesive is an acrylate adhesive.

24. A method according to claim 20, wherein at least a portion of the solid particles are bonded to at least one of the substrates using a low-melting glass.

25. A method according to claim 20, wherein the oligonucleotides fragments are fluorescently-labeled, and are detected as they pass the monitoring point using a fluorescence detector.

26. A method according to claim 25, wherein the fluorescently-labeled oligonucleotides are detected using an argon ion laser.

27. A method according to claim 20, wherein an electric field strength of greater than 150 V/cm is created.

28. A method according to claim 20, wherein an electric field strength of from 250 to 400 V/cm is created.

29. A method according to claim 20, wherein at least a portion of the solid particles are dispersed within the gel in the gel compartment.

30. A loading insert for use in loading a sample onto an electrophoresis gel, comprising
  (a) a substantially rectangular planar base portion having two long edges and two short edges and upper and lower faces;
  (b) a plurality of fingers extending from a first long edge of the base portion in a plane with the upper and lower faces of the base portion, each of said fingers having a width of from 0.5 to 3 mm; said fingers being evenly spaced at intervals of 2 to 7 mm in a region along the first long edge of the base portion starting and ending at a point from 2 to 4 mm from the adjacent short edge of the base portion; and each of said fingers having a tip portion at the distal end thereof, said tip portion being cut with a 30°–60° bevel relative to the plane of the base portion such that the lower surface of each finger is longer than the upper surface.

31. A loading insert according to claim 30, wherein the fingers each have a bevel of 45° at the distal end thereof.

32. A loading insert according to claim 30, wherein lower surface of the loading insert has a plurality of grooves formed therein, said grooves being parallel to the fingers and extending across the entire loading insert.

33. A filling insert for use in filling an electrophoresis gel holder comprising a substantially rectangular planar body member having two long edges and two short edges, and upper and lower faces, wherein
  a first of said long edges is beveled at an angle of from 30 to 60 degrees relative to the plane of the body member such that the lower surface of the body member is larger than the upper surface, and
  a plurality of grooves are formed in the in the lower surface of the body member, said grooves running parallel to the short edges and extending from the one long edge to the other.

* * * * *